United States Patent [19]

Davis, Jr. et al.

[11] Patent Number: 4,486,714

[45] Date of Patent: Dec. 4, 1984

[54] METHOD AND APPARATUS FOR MEASURING RELATIVE PERMEABILITY AND WATER SATURATION OF A CORE OF EARTHEN MATERIAL

[75] Inventors: Lorne A. Davis, Jr.; Dale F. Brost, both of Houston, Tex.

[73] Assignee: Texaco Inc., White Plains, N.Y.

[21] Appl. No.: 406,742

[22] Filed: Sep. 8, 1982

[51] Int. Cl.³ .................. G01V 3/12; E21B 49/02; G01N 27/00

[52] U.S. Cl. ..................................... 324/376; 73/153; 324/58.5 A

[58] Field of Search ............. 324/58 R, 58 A, 58.5 R, 324/58.5 A, 334, 338, 376; 73/153, 38

[56] References Cited

U.S. PATENT DOCUMENTS

| | | | |
|---|---|---|---|
| 2,165,214 | 7/1939 | Blau et al. | 324/58.5 A X |
| 2,963,641 | 12/1960 | Nanz | 324/376 |
| 4,274,283 | 6/1981 | Maus et al. | 73/153 |
| 4,304,122 | 12/1981 | Tentor | 73/153 X |

OTHER PUBLICATIONS

Parsons, R. W., "Microwave Attenuation—A New Tool in Laboratory Flooding Experiments", *Soc. of Petrol. Engineers Journal,* Aug. 1975, vol. 15, pp. 302–309.

*Primary Examiner*—Gerard R. Strecker
*Attorney, Agent, or Firm*—Robert A. Kulason; Ronald G. Gillespie

[57] ABSTRACT

A method of determining the oil and water relative permeabilities and the water saturation of a core of earthen material which includes providing a two phase oil/water liquid to and through said core. The core is irradiated with microwave energy while the liquid is in the core. A received energy signal is generated in accordance with the microwave energy that has passed through the core. A liquid pressure drop along a predetermined length of said core is sensed and a representative pressure drop signal is provided. The oil and water relative permeabilities and the water saturation of the core are derived in accordance with the flow rate of the liquid, the received energy signal and the pressure drop signal. The liquid flow rate may be either sensed or the liquid may be provided at a predetermined flow rate.

9 Claims, 2 Drawing Figures

METHOD AND APPARATUS FOR MEASURING RELATIVE PERMEABILITY AND WATER SATURATION OF A CORE OF EARTHEN MATERIAL

BACKGROUND OF THE INVENTION

Field of The Invention

The present invention relates to meters and monitors measuring characteristics of a core of an earthen material and, more particularly, to meters and monitors measuring the oil and water relative permeabilities and the water saturation of a core of earthen material.

SUMMARY OF THE INVENTION

A method of determining the oil and water relative permeabilities and water saturation of a core of earthen material for a two phase liquid includes providing a two phase oil/water liquid to and through said core. The core is irradiated with microwave energy while the liquid is flowing through it. A received energy signal is generated in accordance with the microwave energy that has passed through the core. A liquid pressure drop along a predetermined length of said core is sensed and a representative pressure drop signal is provided. The relative oil and water permeabilities and the water saturation of the core is derived in accordance with the flow rate of the liquid, the energy signal and the pressure drop signal. The flow rate may be either sensed or the liquid may be provided at a predetermined flow rate.

The objects and advantages of the invention will appear more fully hereinafter, from a consideration of the detailed description which follows, taken together with the accompanying drawings, wherein one embodiment is illustrated by way of example. It is to be expressly understood, however, that the drawings are not for illustrative purposes only, and is not to be construed as defining the limits of the invention.

DESCRIPTION OF THE INVENTION

In the analyses of a petroleum reservoir in an earth formation, one analysis relates to the oil and water relative permeabilities of the reservoir's formation to water saturation of the reservoir's formation. The conventional method of measuring the relative permeabilities to water saturation of a petroleum reservoir in an earth formation involves taking a relatively large size core from the formation and then applying what is known as a steady state relative permeability test. This method depends upon flowing a two phase liquid through the core until a steady state is achieved. The core is removed from the apparatus and weighed after each new steady state is achieved. However, the weight of the core includes the weight of the rock plus the surrounding holder (plastic, epoxy, etc.) and the liquids. The saturations are determined by the small weight differences due to the density difference between oil and water. This difference is enhanced by using a light oil and heavy water with a lot of salt in it. Not only is this method subject to error because of the small weight difference due to the density difference while measuring heavier weighted objects, but also that each removal of the core increases the chance for liquid drainage and the introduction of air into the core.

The present invention increases substantially the accuracy while speeding up the time of testing and further improves upon the testing by being able to utilize the same type of crude oil that is present in the reservoir and the same density of brine that would be used in the reservoir. Further, the conventional steady state relative permeability method can only be used at room temperature because of the disassembling process while the present invention can be used at temperatures more in keeping with the reservoir temperature.

Figure 1:
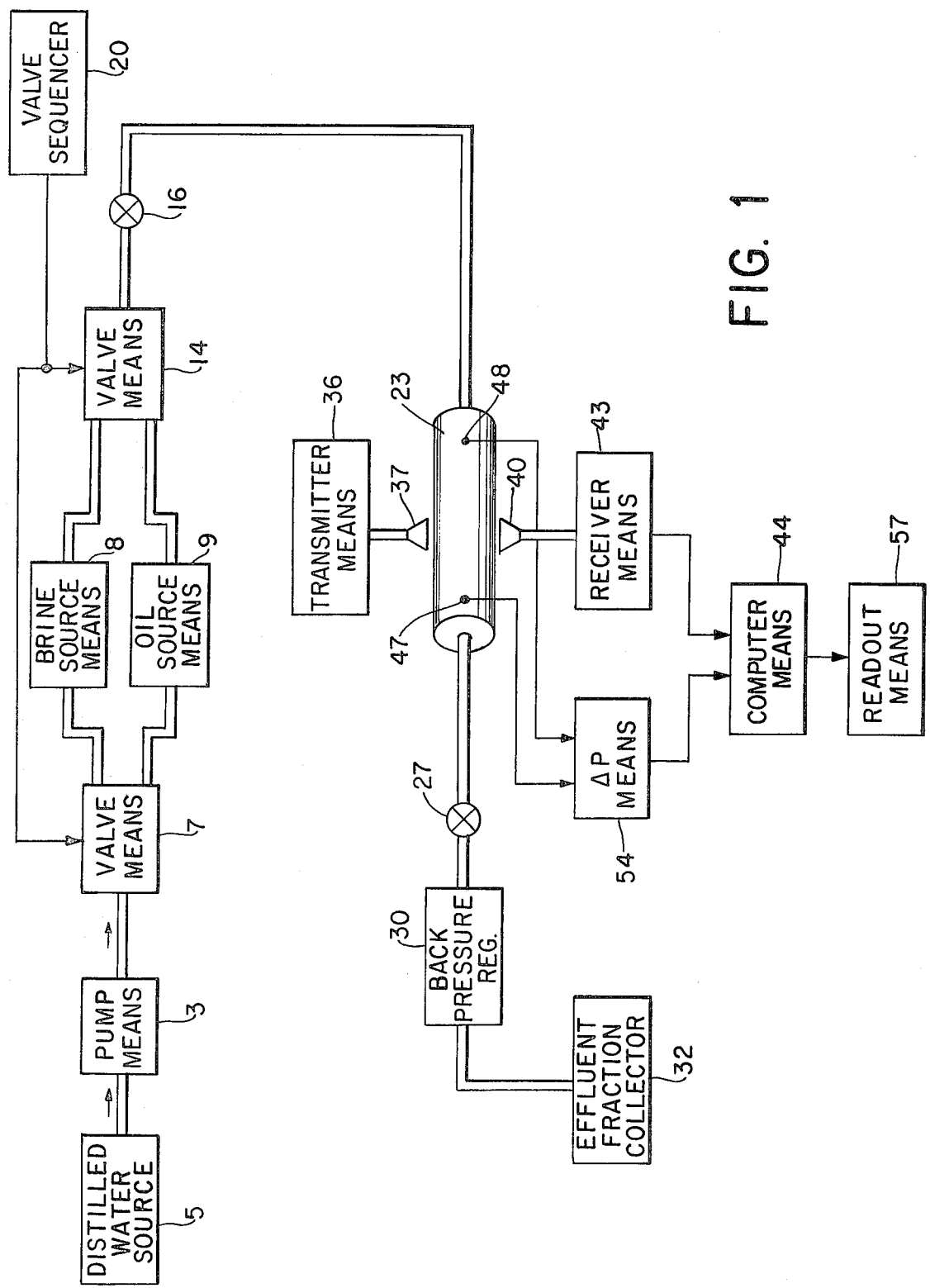
FIG. 1 is a simplified block diagram of apparatus, constructed in accordance with the present invention, for measuring the oil and water relative permeabilities and the water saturation of a core of earthen material.

Referring now to FIG. 1, pump means 3 pumps distilled water from a distilled water source 5 to valve means 7, which is controlled as hereinafter explained, to provide the distilled water to brine source means 8 or to oil source means 9. The volume flow rate of pump means 3 may be controlled. Brine source means 8 and oil source means 9 each includes a conventional type free floating piston (not shown) in a container (not shown) having brine and crude oil respectively. The pumped in distilled water causes the piston to expel the brine from brine source means 8 and the crude oil from oil source means 9 to valve means 14. Cooperation of valve means 7 and 14, in response to control signals from a valve sequencer 20 provides either the brine or the crude oil to a valve 16. Valve sequencer 20 may be of the type manufactured by Valco Instruments Company as their part number DVSP-4. Valve means 7 and 14 may be of the type made by Beckman Instruments, Inc. as their part number 243303. Valve means 7 and 14 are in essence rotary valves, rotating step wise in accordance with a signal from valve sequencer 20 to alternately pass brine and oil to valve 16. The quantities of brine or crude oil are changed by programming valve sequencer 20 accordingly.

The utilization of valve means 7 and 14 and valve sequencer 20 is such as to introduce a two phase liquid to a test cell 23 containing a core 24 (shown in FIG. 2) of the earthen material from the petroleum reservoir in question by way of valve 16. In order for valve means 7 and 14 to establish a uniform two phase liquid, it is preferred that valve means 7 and 14 be switched often enough so that the period of one complete cycle of valve means 7 and 14 is substantially less than the time it takes for a front of the liquid to move through test cell 23 in one phase flow. This restriction merely keeps saturation fluctuations minimal. Preferably, the period of the cycle for a two phase liquid is considerably smaller than 30 minutes.

The liquid flow through test cell 23 is provided to a valve 27 which in turn is provided to an optional piece of apparatus namely backpressure regulator 30. Valves 16, 27, cooperate to permit the removal of test cell 23 for cleaning and other preparation activities. The effluent passes through backpressure regulator 30 and is provided to an effluent fraction collector 32.

While the two phase liquid is flowing through test cell 23, transmitter means 36 provides electromagnetic energy at a microwave frequency; said electromagnetic energy hereinafter shall be referred to as microwave energy. The microwave energy from transmitter means 36 is provided to an antenna 37 which radiates the microwave energy through test cell 23, and hence through core 24 within. The microwave energy that is passed through core 24 is received by an antenna 40 which provides the received microwave energy to receiver means 43. Receiver means 43 provides an electrical signal to computer means 44 in accordance with the received microwave energy. Pressure sensors 47, 48 are affixed to test cell 23 spaced a predetermined distance apart, in such a manner so as to sense the pressures at those locations on the surface of core 24 and provides corresponding signals to differential pressure means 54. Differential pressure means 54 in turn provides a signal to computer means 44 corresponding to the pressure drop across the predetermined distance of core 24. Computer means 44 provides an output signal corresponding to the relative permeabilities and the water saturation of core 24 for the two phase liquid passing through it to readout means 57 in accordance with the signal from receiver means 43 and the signal from differential pressure means 54.

Figure 2:
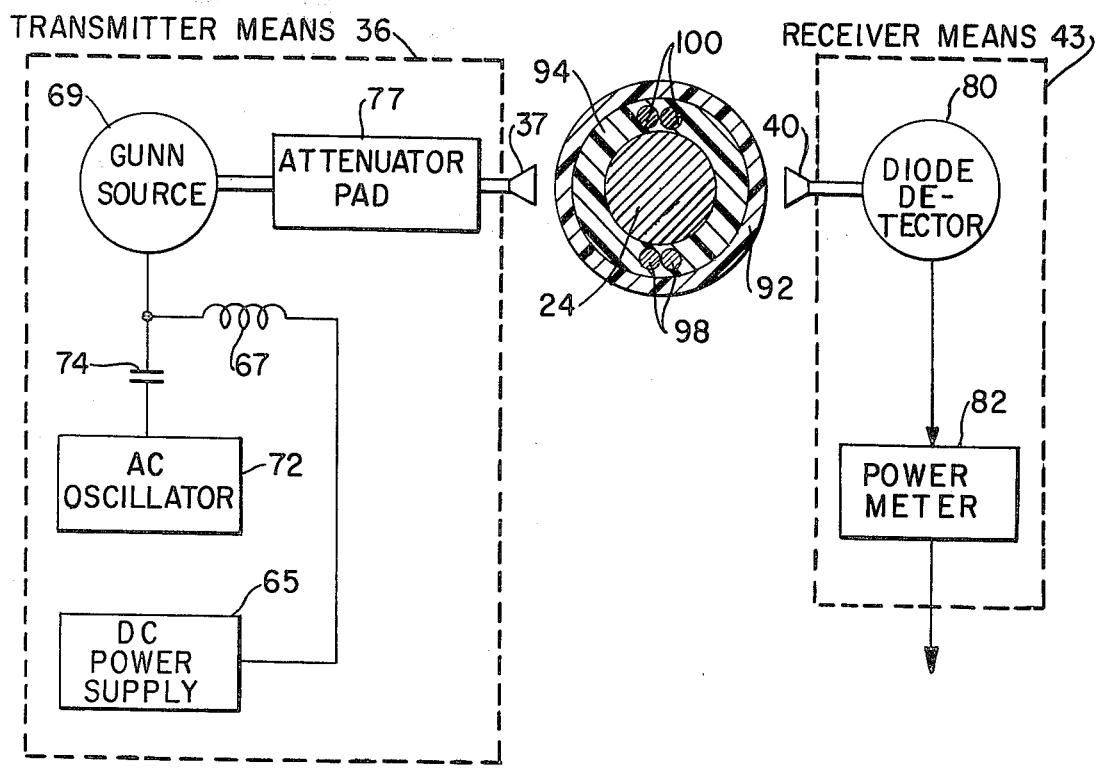
FIG. 2 is a detailed diagram of the transmitter means, the receiver means, and the test cell shown in FIG. 1.

Referring now to FIG. 2, transmitter means 36 includes a direct current power supply 65 which provides DC power through a coil 67 to a Gunn microwave source 69 of the type that is manufactured by Racon, Inc. as their part number 10014-102-02. An oscillator 72 provides an AC voltage as a predetermined frequency through a capacitor 74 to Gunn source 69. A preferred frequency of the AC voltage is 1 KHz. Gunn source 69 provides the microwave energy, at a preferred frequency of 10.525 GHz, whose amplitude oscillates at the 1 KHz frequency. Source 69 provides the microwave energy to an attenuator pad 77 which provides the microwave energy in turn to horn antenna 37. It should be noted that a horn antenna is used because the Gunn source 69 is being operated in an X-band mode. It may be desired to operate Gunn source 69 at a preferred frequency of 24.125 GHz, which is in the K-band mode and makes monitoring more independent of temperature and salinity in regards to the liquid in test cell 23. The determination of whether to use X-band or K-band is also in part determined by the core size selected. A preferred power output for the X-band is 10mw while for the K-band is anything greater than 50mw to safe operating levels. Horn antenna 37 is replaced by a dielectric rod antenna and Gunn source 69 is of a type similar to that manufactured by Plessey Optoelectronics and Microwave Ltd., as their part GD0131 when operating in a K-band mode. Further, oscillator 72 may be omitted in K-band operations.

The microwave energy passing through sample cell 23 is received by another horn antenna 40 in X-band mode, or a dielectric rod antenna in the K-band mode, and provided to a diode detector 80 in receiver means 43. Diode detector 80 provides an electrical signal, corresponding to the detected microwave energy, to a power meter 82 which in turn provides the output signal to computer means 44.

Test cell 23 includes a cylindrical core 24 of an earth formation, having a preferred diameter in the range of from a ½ inch to ¾ inch and a preferred length of approximately 4 inches, and is maintained in a hard plastic tubular shell 92 by epoxy 94. Shell 92 may be made of a machineable hard plastic such as chlorinatedpolyvinylchloride or polyvinylidinedifluoride. Embedded in epoxy 94 are microwave absorber rods 98 and 100. In one particular application there are four such microwave absorber rods. One pair of absorber rods 98 is located along side of core 24 while another pair of absorber rods 100 is located diametrically opposite along side of core 24. It should be noted that core 24 is preferably oriented with relation to antennas 37 and 40 in a manner so that a straight line from antenna 37 to antenna 40 is substantially perpendicular to an axis passing through both pairs of absorber rods 98, 100. Absorber rods 98, 100 prevents the microwave energy from circumventing core 24 and being detected by diode detector 80 so as not to cause erroneous readings and so that the microwave energy detected by detector 80 is the microwave energy that has passed through core 24. Microwave absorber rods 98, 100 are made of ferrite loaded epoxy. Preferred attenuation coefficient for such material is 46 dB/cm at 10 GHz.

A more detailed construction of test cell 23 is disclosed in greater detail, with the appropriate fittings which are well known to one in the art, in U.S. application Ser. No. 336,136, filed Dec. 31, 1981, assigned to Texaco Inc., assignee of the present invention. Test cell 23 of that construction has been modified to provide for pressure sensors 47 and 48 to be mounted thereon to sense the pressure in core 24. It is preferred that core 24 is obtained from the same earthen formation that contains the petroleum reservoir. With the length of core 24 being 4 inches long and pressure sensors 47 and 48 being 3 inches apart, it is preferred that sensors 47, 48, be located a half inch in from the nearest end. The distance of the half inch eliminates end effects. The distance of 3 inches may also be changed, the main objectives in placement of pressure sensors 47, 48 are to have a substantial length between pressure sensors 47, 48 and to avoid end effects.

Computer means 44 basically solves the Darcy's equation set forth as follows.

1. $Qo = (K)(Kro)[\Delta pA/\mu oL]$ and
2. $Qw = (K)(Krw)[\Delta pA/\mu wL]$ where Qo and Qw are the volume flow rates of the oil and the water respectively, in cm³/sec., K is the absolute permeability of core 24 to single phase liquid flow in darcies, Kro and Krw are the relative permeabilities of core 24 to oil and water, respectively, L is the distance between pressure sensors 47 and 48 in cm, Δp is the pressure drop of the fluid along the length L in atm, A is the cross sectional area of core 24 in cm², and μo and μw are viscosities of the oil and water, respectively, in cp at test conditions.

The values for Qo and Qw are determined from the following equations

3. $Qo = f_o Q_T$, and

4. $Qw = f_w Q_T$, where QT is the total volume flow rate of the two phase liquid which may be predetermined by controlling pump 3 or it may be sensed; and $f_o$ and $f_w$ are dimensionless fractional volume flow rates and are predetermined, and hence known from the programming of valve sequencer 20.

The foregoing relates to the basic method and apparatus for measuring the oil and water relative permeabilities and the water saturation. However, the procedure is more detailed than previously set forth and is as follows. It will be assumed that at the start of each test that core 24 has been cleaned and evacuated. The calibration is as set forth in the aforementioned U.S. application but will be repeated here at the cost of being repetitious. Initially microwave transmitter 36 radiates core 24 in test cell 23 while core 24 has no liquid in it so that a first test value is entered into computer means 44 by receiver means 43. To the microwave equipment it is as if core 24 were filled only with oil and thus this first test value corresponds to an oil filled core reading.

Pump means 3, distilled water source 5, brine source means 8, valve means 14, and valve sequencer 20 are operated to fill core 24 of test cell 23 with brine. When the brine is observed entering effluent fraction collector 32, a second reading provided by receiver means 33 is entered into computer means 44 and is indicative of the salt water in core 24. In the third calibration step, valve sequencer 20 is operated in the manner so that valve means 14 blocks the brine but passes the oil from oil source means 9 and pump means 3 is operated until only crude oil enters effluent fraction collector 32. A third reading provided by receiver means 43 at this time is representative of residual brine-to-oil injection.

Pump means 3 is again activated and valve sequencer 20 controls valve means 14 to pass brine from brine source means 8 to test cell 23 until only salt water enters effluent fraction collector 32. A fourth measurement at this time corresponds to residual oil-to-water-flood. Further, each time at the end of the third and fourth calibration readings, a conventional material balance is carried out to determine the oil saturation measurements for the conditions of those two steps. That information is also entered into computer means 44. Computer means 44 in effect establishes a calibration curve from the data of the calibration process and determines the water saturation from the received microwave energy and its relation to the curve.

At this point, test cell 23 is removed from the test system and again cleaned by flushing with distilled water, then isopropyl alcohol, then toluene, then isopropyl alcohol, then distilled water and finally flushed with reservoir brine and returned to the test apparatus. Of course it will be obvious to one skilled in the art that distilled water may also be pumped directly into test cell 23 with proper valve control and that the other cleaning fluid may also be used for in-system cleaning of core 24 if so desired. With test cell 23 back in the test system and ready for testing, a single phase injection mode is initiated. This simply means that the system is operated so that only oil source means 9 is providing oil to test cell 23 and this represents the 100% fraction of oil and zero percent fraction of water of the injection liquid. Transmitter means 36, receiver means 43 and computer means 44 are then operated to determine the relative permeability $K_{ro}$ of core 24 for oil. The relative permeability $K_{rw}$ of core 24 for water during this step is zero. Computer means 44 does this in accordance with the preprogrammed Darcy's equations 1 and 2 hereinbefore mentioned using the sensed pressure differential $\Delta p$ and the water saturation $S_w$ obtained from the output from receiver means 43 and computer means provides an output to readout means 57 for showing $K_{ro}$ and $S_w$.

The test system is again operated but this time the programming of valve sequencer 20 controls valve means 14 to provide two phase liquid having 98% crude oil and 2% brine. Again $\Delta p$ and water saturation $S_w$ are measured and the relative permeabilities $K_{ro}$ and $K_{rw}$ for oil and water, respectively, are computed by computer means 44. These operations are repeated for various ratios of brine and crude and are usually done in ascending percentage values of brine. After the step involving 100% brine is reached, all of the steps are then repeated with a descending percentage of brine, starting with 100% brine injection liquid and ending with zero percent brine injection liquid. The reverse order of percentage of brine allows for hysteresis of core 24 in response to the changing of the injection liquid.

The present invention may even be used at simulated field conditions of temperature to determine the oil and water permeabilities and the water saturation of a petroleum reservoir formation. The present invention as hereinbefore described can stand up to 300 psi of pressure. The present invention may also be used in an oven and the temperature raised to simulate reservoir temperature. However, it should be noted that if the test temperature is close to or greater than the temperature ratings of the components of the microwave system, then an oven may be constructed in which only sample cell 23 is located in the oven and the microwave energy is directed through the walls of the oven and through sample cell 23.

What is claimed is:

1. A method of determining the oil and water relative permeabilities and the water saturation of a core of earthen material comprising the steps of:

providing a two phase oil/water liquid to and through the core, irradiating said core with microwave energy with the liquid in the core, receiving the microwave energy that has passed through the core, determining the water saturation of the core in accordance with the received microwave energy, sensing the pressure drop of the liquid along the predetermined length of the core, and determining the oil and water relative permeabilities of the core in accordance with properties of the core, the oil fraction of the liquid, the water fraction of the liquid, and the flow rate of the liquid.

2. A method as described in claim 1 in which the determining the relative permeabilities step includes determining the relative permeabilities in accordance with the following equations:

1. $Q_o = (K)(K_{ro})[\Delta p A / \mu_o L]$,

2. $Q_w = (K)(K_{rw})[\Delta p A / \mu_w L]$,

3. $Q_o = f_o Q_T$, and

4. $Q_w = f_w Q_T$ where $Q_T$, $Q_o$ and $Q_w$ are the total volume flow rate of the liquid, the volume flow rate of the oil and the volume flow rate of the water, respectively; K, $K_{ro}$ and $K_{rw}$ are the core's absolute permeability, relative permeability to oil and relative permeability to water, respectively; $\mu_o$ and $\mu_w$ are the viscosities of the oil and water, respectively; $\Delta p$ is the pressure drop along the predetermined length of the core; A and L are the cross-sectional area of the core and the predetermined length of the core, respectively; and $f_o$ and $f_w$ are fractional volume flow rates of the oil and the water, respectively.

3. A method as described in claim 2 in which the liquid is provided at a predetermined flow rate.

4. A method as described in claim 3 in which the providing of a two phase oil/water liquid includes alternately providing oil and water in small fractions and in which the period of providing one fraction of oil and one fraction of water is substantially less than the time necessary for a front of the liquid to move through the length of the core.

5. A method as described in claim 2 in which the flow rate of the liquid is sensed to determine the flow rate.

6. Apparatus for determining the oil and water permeabilities and the water saturation of a core of earthen material comprising:
a test cell containing the core,
means for irradiating the test cell with microwave energy,
means for receiving microwave energy that has passed through the core in the test cell and providing a signal corresponding to the received microwave energy,
means for sensing a pressure drop along a predetermined length of the core in the test cell and providing a signal representative thereof,
means connected to the pressure drop sensing means and to the receiver means for determining the oil and water relative permeabilities of the core in accordance with the sensed pressure drop and the flow rate of the liquid and for determining the water saturation of the core in accordance with the signal from the receiver means.

7. Apparatus as described in claim 6 in which the relative permeability determining means determines the oil and water permeabilities in accordance with the following equations:

1. $Q_o = (K)(K_{ro})[\Delta pA/\mu_o L]$,

2. $Q_w = (k)(K_{rw})[\Delta pA/\mu_w L]$,

3. $Q_o = f_o Q_T$, and

4. $Q_w = f_w Q_T$ where $Q_T$, $Q_o$ and $Q_w$ are the total volume flow rate of the liquid, the volume flow rate of the oil and the volume flow rate of the water, respectively; K, Kro and Krw are the core's absolute permeability, relative permeability to oil and relative permeability to water, respectively; $\mu_o$ and $\mu_w$ are the viscosities of the oil and water, respectively; $\Delta p$ is the pressure drop along the predetermined length of the core; A and L are the cross-sectional area of the core and the predetermined length of the core, respectively; and fo and fw are fractional volume flow rates of the oil and the water, respectively.

8. Apparatus as described in claim 2 in which the means for providing the two phase liquid includes:
a source of brine,
a source of crude oil,
valve means connected to the brine source and the oil source and responsive to a control signal for passing either the brine or the crude oil,
pump means connected to the brine source and the oil source for pumping the brine and the crude oil to the valve means, and
valve sequencer means for controlling the valve means to alternately pass the brine and the crude oil.

9. Apparatus as described in claim 8 in which the valve sequencer means controls the valve means in the manner to alternately pass brine and crude oil at a frequency such that the period of one cycle of brine and oil is substantially less than the time for a front of the liquid to pass through the core.

* * * * *